United States Patent [19]

Iwai et al.

[11] Patent Number: 4,849,404
[45] Date of Patent: * Jul. 18, 1989

[54] THERAPEUTIC AND PROPHYLACTIC AGENT FOR GASTROINTESTINAL ULCERS

[75] Inventors: Masakazu Iwai, Fujiidera; Kazumasa Yokoyama, Toyonaka; Tsunekazu Fukushima, Kobe, all of Japan

[73] Assignee: The Green Cross Corporation, Osaka, Japan

[*] Notice: The portion of the term of this patent subsequent to May 31, 2005 has been disclaimed.

[21] Appl. No.: 163,732

[22] Filed: Mar. 3, 1988

Related U.S. Application Data

[60] Division of Ser. No. 827,209, Feb. 4, 1986, Pat. No. 4,748,157, which is a continuation of Ser. No. 626,421, Jun. 29, 1984, abandoned.

[30] Foreign Application Priority Data

Jul. 4, 1983 [JP] Japan .................................. 58-121756
Jul. 4, 1983 [JP] Japan .................................. 58-121757

[51] Int. Cl.[4] ............................................ A61K 37/18
[52] U.S. Cl. ........................................ 514/2; 530/388; 514/929; 514/926; 514/927
[58] Field of Search ................... 514/2, 925, 926, 927; 530/388

[56] References Cited

U.S. PATENT DOCUMENTS 4,330,620 5/1982 Gruber et al. ........................ 435/7

FOREIGN PATENT DOCUMENTS 122132 10/1984 European Pat. Off. .

OTHER PUBLICATIONS

Chem. Abst. 99:68657u, 1983.
Chemical Abstracts, vol. 99, No. 9, 29th Aug. 1983; M. Tsutomo, "Studies of Pharmalogical Activation . . . ".
Chem. Abstracts, citation of Green Cross Corp., vol. 96:205420r, 1982.

*Primary Examiner*—John W. Rollins
*Attorney, Agent, or Firm*—Cushman, Darby & Cushman

[57] ABSTRACT

Fab or Fc fragment of human IgG which is obtainable by enzymatic digestion of the human IgG is reduced by a reducing agent to sever an interchain of disulfide bonds therein and then blocked the SH radicals formed with alkyl group which may contain other groups. The resulting alkylated Fab and Fc fragments display therapeutic and prophylactic action for gastrointestinal ulcers by the oral or parenteral administration.

6 Claims, No Drawings

THERAPEUTIC AND PROPHYLACTIC AGENT FOR GASTROINTESTINAL ULCERS

This is a division of application Ser. No. 827,209, filed Feb. 4, 1986, now U.S. Pat. No. 4,748,157, which is a continuation of Ser. No. 626,421, filed June 29, 1984, now abandoned.

This invention relates to a therapeutic and prophylactic agent for gastrointestinal ulcers which comprises, as the principal ingredient, alkylated Fab or Fc fragment of human IgG (hereinafter referred to simply as alkylated Fab or Fc fragment).

The pharmacological action and pharmaceutical application of the alkylated Fab or Fc fragment were not known previously, and hence they have never been used as a medicine. The inventors have found out, for the first time, that the alkylated Fab or Fc fragment can be used as a therapeutic and prophylactic agent for gastrointestinal ulcers and accomplished this invention on the basis of the finding.

The Fab and Fc fragments of human IgG have already been reported as a fragment constituting the publicly known IgG in, for example, a paper of Porter et al. [Biochem. J., 73, 119 (1959)]. Both Fab and Fc fragments of human IgG are polypeptides which have a molecular weight of from 45,000 to 50,000 and can be obtained by digestion of human-origin IgG with papain or plasmin. The two fragments are differentiated from each other in the behaviors of the development in an ion-exchanger which has adsorbed the both fragments, and the method of their recovery has already been established by Porter et al. mentioned abvoe.

The alkylated Fab or Fc fragment which is specified as the effective ingredient in this invention can be obtained by the reduction of the interchain of disulfide bonds in Fab or Fc fragment of human IgG, followed by alkylation.

The alkylated Fab or Fc fragment according to this invention is obtained typically as outlined below.

A solution containing IgG (protein concentration of 2 to 10%) is adjusted to pH 6 to 9, mixed with plasmin or papain, and the mixture is treated at 20° to 40° C. for 10 to 30 hours. The insolubles are discarded from the reaction mixtures, and the insolubles-freed liquid is subjected to gel filtration to separate undigested IgG from the digestion product. The latter is chromatographed by the use of an ion exchanger (CM-cellulose or DEAE-cellulose) whereby the Fab and Fc fragment of human IgG are selectively adsorbed and then eluted so that the Fab is recovered prior to the Fc.

After beng recovered, both fragments (Fab and Fc) of human IgG are reduced with a proper reducing agent to sever disulfide bonds and then alkylated to give the alkylated Fab and Fc fragments, respectively.

Examples of reducing agents for use in this invention include 2-mercaptoethanol, dithiothreitol and dithioerythritol. They are used in an amount corresponding to a final concentration of 0.01 to 0.068M.

The alkylated fragments can be prepared by blocking the SH radicals resulted from cleavage of the disulfide bonds of the interchain of each fragment in a conventional manner [Biochemistry, 7 (5), 1950–1958 (1968)]. Examples of groups used for blocking the SH radicals are as follows.

(1) Lower alkyl groups: methyl, ethyl, n-propyl and so forth, (2) N,N-Dilower-alkylcarbamide-lower-alkyl group: N,N-diethylcarbamidemethyl and so forth, (3) Lower-alkoxycarbonyl-lower-alkyl group: ethoxycarbonylmethyl, ethoxycarbonylethyl and so forth, (4) Carboxy-lower-alkyl group: carboxymethyl, carboxyethyl and so forth, (5) Carbamoyl-lower-alkyl group: carbamoylmethyl and so forth, (6) Cyano-lower-alkyl group: cyanomethyl and so forth, (7) ω-Amino-lower alkyl group: $-CH_2CH_2NH_2$ and so forth, (8) Benzoyl-lower alkyl group: $-CH_2COC_6H_5$ and so forth.

Thus, it will be noted that the word "alkylated" mentioned in the specification and Claims attached means to be linked not always with an alkyl in normal sense but also an alkyl accompanying other groups, such as carbamide, carbonyl, carboxy, carbamoyl cyano and amino.

These SH radical blocked products can be prepared by a method known per se or in a manner similar thereto, using a reactive derivative of a compound having the above mentioned blocking group, in which a reactive group is attached to the lower alkyl group. Examples of the reactive group are a halogen such as iodine, bromine and chlorine atom.

The lower alkyl in the blocking group is one having 1 to 3 carbon atoms.

Hereunder are described the experiments which were performed to confirm the pharmacological action and effect, acute toxicity, dose and method of administration of the alkylated Fab and Fc fragments in this invention.

(1) Pharmacological action and effect.

Anti-ulcerogenic activity of the alkylated Fab and Fc fragment was examined by using experimental ulcered rats induced by (a) pylorus ligation or (b) phenylbutazone administration (P.O.).

(a) According the pylorus ligated ulceration was produced according to the method of Shay et al. [Gastroenterology, 5, 43 (1945)]. Wistar-strain male rats weighing 200 to 250 g were deprived of food for 24 hours, and then the stomachs were excised from the rats under anesthesia with ethyl ether. The ulcers developed in the forestomachs were inspected and evaluated in terms of the following ulcer index according to the method of Narumi et al. [J. Takeda Res. Lab., 29, 85 (1970)]:

0: normal
1: erosion or hemorrhagic spot
2: 10 or less small ulcers (1 mm or less in diameter)
3: 10 or more small ulcers; or 10 or less medium-sized ulcers (2 to 4 mm in diameter)
4: 10 or more medium-sized or large ulcers (4 mm or more in diameter)
5: perforation The specimen used in this experiment is the one prepared in Reference Example 1 described later. It was dissolved in a sterile physiological saline and administered intravenously twice, immediately and 8 hours after the ligature, at doses indicated in Tables 1 (1) and 1 (b).

(b) The phenylbutazone-induced ulcer was produced according to the method of Suzuki et al. [Japan. J. Pharmaco., 26, 471 (1976)].

Wistar-strain male rats weighing 150 to 200 g were deprived of food for 24 hours. Then the alkylated Fab and Fc fragment prepared in Reference Example 1, respectively, was administered intravenously to the animals at doses indicated in Tables 2 (a) and 2 (b), followed, after 30 minutes, by oral administration of 200 mg/kg of phenylbutazone (suspended in 5% gum arabic solution. The rats were deprived of food and water for further 5 hours; then the stomachs were excised from the animals under anesthesia with ethyl ether, and fixed in formalin. The ulcers developed in the glandular portion of stomach were inspected and evaluated in terms of the "ulcer index" which was defined as the sum of the following "score".

Score 1: longest diameter of ulcer 1 mm
Score 2: 1 to 2 mm
Score 3: 2 to 3 mm
Score 4: 3 to 4 mm
Score 5: 4 to 5 mm
Score 10: >5 mm
Score 25: perforation The results obtained in (a) and (b) were shown in Tables 1 and 2, respectively.

With respect to the action of the alkylated fragments against the pylorus ligated ulcer, Tables 1 (a) and 1 (b) reveal that with twice administration of 10 mg/kg of each fragment, they inhibit the development rate of ulcer formation by about 77% in case of Fab and about 74% in case of Fc, as compared with the physiological saline injected group (Control). Even with twice administration of a smaller does of 5 mg/kg, an inhibitory activity of 49% is observed in alkylatd fragment Fab and of 50% is observed in alkylated Fc fragment.

TABLE 1 (a)

| Treatment | Dose (mg/kg) × times | Number of animals | Ulcer index | Inhibition rate (%) |
|---|---|---|---|---|
| Control (Physiological saline) | — | 10 | 3.5 ± 0.4[a] | — |
| Native IgG | 10 × 2 | 10 | 3.4 ± 0.5 | 2.8 |
| Fab fragment | 10 × 2 | 10 | 3.1 ± 0.5 | 11.4 |
|  | 5 × 2 | 10 | 3.3 ± 0.4 | 5.7 |
|  | 1 × 2 | 10 | 3.4 ± 0.3 | 2.9 |
| Alkylated Fab fragment | 10 × 2 | 10 | **0.8 ± 0.2 | 77.1 |
|  | 5 × 2 | 10 | **1.8 ± 0.2 | 48.6 |
|  | 1 × 2 | 10 | *3.0 ± 0.3 | 14.3 |
| Atropine sulfate | 5 × 2 | 10 | **1.5 ± 0.2 | 57.1 |
|  | 1 × 2 | 10 | **2.2 ± 0.4 | 37.1 |

Note: [a]Mean ± standard error (*p < 0.01, **P < 0.001)

TABLE 1 (b)

| Treatment | Dose (mg/kg) × times | Number of animals | Ulcer index | Inhibition rate (%) |
|---|---|---|---|---|
| Control (Physiological saline) | — | 10 | 4.2 ± 0.4[a] | — |
| Native IgG | 10 × 2 | 10 | 4.1 ± 0.5 | 2.8 |
| Fc fragment | 10 × 2 | 10 | *3.6 ± 0.5 | 14.3 |
|  | 5 × 2 | 10 | 3.9 ± 0.3 | 7.1 |
|  | 1 × 2 | 10 | 4.1 ± 0.5 | 2.4 |
| Alkylated Fc fragment | 10 × 2 | 10 | **1.1 ± 0.2 | 73.8 |
|  | 5 × 2 | 10 | **2.1 ± 0.3 | 50.0 |
|  | 1 × 2 | 10 | *3.4 ± 0.4 | 19.0 |
| Atropine sulfate | 5 × 2 | 10 | **1.7 ± 0.3 | 59.5 |
|  | 1 × 2 | 10 | **2.5 ± 0.4 | 40.5 |

Note: [a]Mean ± standard error (*p < 0.01, **P < 0.001)

Tables 2 (a) and 2 (b) reveal that the alkylated fragments have statistically significant inhibitory activities of about 61% in the alkylated Fab fragment and of about 73% in the alkylated Fc fragment against control group in phenylbutazone-induced ulceration at a dose of 10 mg/kg of each fragment.

TABLE 2 (a)

| Treatment | Dose (mg/kg) | Number of animals | Ulcer index | Inhibition rate (%) |
|---|---|---|---|---|
| Control (Physiological saline) | — | 10 | 15.8 ± 4.7[a] | — |
| Alkylated Fab fragment | 10 | 10 | *6.2 ± 1.1 | 60.8 |
| Atropine sulfate | 5 | 10 | *2.8 ± 0.6 | 82.3 |

Note: [a]Mean ± standard error (*P < 0.001)

TABLE 2 (b)

| Treatment | Dose (mg/kg) | Number of animals | Ulcer index | Inhibition rate (%) |
|---|---|---|---|---|
| Control (Physiological saline) | — | 10 | 21.1 ± 4.4[a] | — |
| Alkylated Fc fragment | 10 | 10 | *5.8 ± 1.5 | 72.5 |
| Atropine sulfate | 5 | 10 | *3.3 ± 1.2 | 84.4 |

Note: [a]Mean ± standard error (*P < 0.001)

(2) Pharmacological action

Studies were made to clarify the mechanism of anti-ulcer action of the alkylated Fab and Fc fragments.

(a) The inhibitory action of the alkylated fragments on gastric-juice secretion was investigated. The products obtained in Reference Example 1 which will be described later were each dissolved in physiological saline and administered intravenously.

The inhibitory action on gastric-juice secretion was determined according to the method of Shay et al. [Gastroenterology. 26, 906 (1954)]. Thus, Wistar-strain male rats weighing 150 to 200 g were deprived of food for 48 hours and the pylorus of each animal was ligated. Four hours after the ligation, the retained gastric juice was collected and determined its volume, total acid output and total peptic activity. The total acid output was determined by titration with 1/50N NaOH solution, phenolphthalein being used as the indicator. The total peptic activity was determined according to the method of Anson [Brit. J. Pharmacol., 13, 54 (1958)] with casein used as the substrate. The specimens (the alkylated products, Fab and Fe fragments obtained and IgG used in Reference Example 1 were each dissolved in sterile physiological saline and administered intravenously through the tail vein of rat immediately after ligation.

The results were shown in Tables 3 (a) and 3 (b). In comparison with the volume of gastric juice in the control group, the administration of the two alkylated fragments at a dose of 10 mg/kg showed an inhibition of about 75% in Fab fragment and of about 70% in Fc fragment, and a statistically significant inhibition was observed even at a dose of 5 mg/kg in both fragments. Similar inhibitions were observed also in the total acid output and in the total peptic activity.

TABLE 3 (a)

| Treatment | Dose (mg/kg) | Number of animals | Gastric-juice volume (ml/100 g body weight) |
|---|---|---|---|
| Control | — | 7 | 2.55 ± 1.04[a] |

TABLE 3 (a)-continued

| Treatment | Dose (mg/kg) | Number of animals | Gastric-juice volume (ml/100 g body weight) |
|---|---|---|---|
| (Physiological saline) | | | |
| Native IgG | 10 | 7 | 2.53 ± 0.80 |
| Fab fragment | 10 | 7 | *1.48 ± 0.47 |
| | 5 | 7 | 1.85 ± 0.73 |
| Alkylated Fab fragment | 10 | 7 | ***0.64 ± 0.36 |
| | 5 | 7 | **1.05 ± 0.50 |

| Total acid output (μEq/100 g body weight) | Total peptic activity (mg as tyrosine/ 100 g body weight) |
|---|---|
| 304.3 ± 138.5(a) | 185.2 ± 57.9(a) |
| 310.2 ± 58.8 | 180.3 ± 38.9 |
| *169.2 ± 43.6 | *123.4 ± 27.9 |
| 225.4 ± 50.8 | 158.8 ± 36.7 |
| ***68.6 ± 45.6 | ***69.7 ± 28.5 |
| **101.5 ± 28.8 | **92.6 ± 30.1 |

Note: (a)Mean ± standard error (*P < 0.01, ***P < 0.001)

TABLE 3 (b)

| Treatment | Dose (mg/kg) | Number of animals | Gastric-juice volume (ml/100 g body weight) |
|---|---|---|---|
| Control (Physiological saline) | — | 7 | 3.46 ± 0.81(a) |
| Native IgG | 10 | 7 | 3.40 ± 0.53 |
| Fc fragment | 10 | 7 | *2.39 ± 0.93 |
| | 5 | 7 | 2.77 ± 1.07 |
| Alkylated Fc fragment | 10 | 7 | **1.08 ± 0.78 |
| | 5 | 7 | **1.42 ± 0.61 |

| Total acid output (μEq/100 g body weight) | Total peptic activity (mg as tyrosine/ 100 g body weight) |
|---|---|
| 428.5 ± 110.4(a) | 235.2 ± 63.4(a) |
| 418.1 ± 80.3 | 230.7 ± 56.2 |
| *305.8 ± 46.3 | *158.7 ± 49.7 |
| 330.0 ± 97.2 | 176.4 ± 50.5 |
| **108.8 ± 39.7 | **68.6 ± 15.7 |
| **162.8 ± 47.8 | **94.1 ± 18.3 |

Note: (a)Mean ± standard error (*P < 0.05, **P < 0.001)

(3) Dose and method of administration

Judging from the test results mentioned above, the alkylated Fab and Fc fragments are preferably administered at a dose of 1 to 100 mg/kg/day for adult.

This medicine can be administered either as injections or by oral route. For injection, it is used, for example, after dissolved in distilled water for injection or the like at the time of using. It is administered intravenously or intramuscularly. For oral use, it is administered in the form of capsules, tablets, powders, liposome preparations, liquid preparations for oral administration, etc. These can be prepared according to methods known to those skilled in the art as, for example, are described in Japanese Pharmacopoeia.

The therapeutic and prophylactic agent for gastrointestinal ulcers comprising, as its principal ingredient, the alkylated fragments of this invention have an extremely low toxicity and exhibit a marked pharmacological effect, so that they are very effective as a therapeutic and prophylactic medicine for ulcers.

This invention will be further illustrated below with reference to Reference Examples and Examples. Reference Example 1 (Digestion with plasmin)

To 60 ml of a 3% solution of IgG, was added 60 mg of sodium azide, and the mixture was adjusted to ph 7.5 with 1n NaOH soution. Plasmin was added to the above mixture to give a final concentration of 4 cu/ml, and digestion was carried out at 35° C. for about 15 hours. After completion of the digestion, the resultant mixture was adjusted to pH 6.5, allowed to stand at 4° C. for 1 hour and then centrifuged to remove insolubles. About 60 ml of the plasmin-digested liquid was subjected to gel filtration by using a Sephadex ® G-200 column to separate the undigested globulin (7S) from the digested product (Fab+Fc). The digested product solution pooled was dialyzed against 0.01M phosphate buffer solution (pH 7.0) at 4° C. over a night. After insolubles formed were removed, it was poured slowly into CM-cellulose column which had been equilibrated with the same phosphate buffer solution. The column was washed with the same phosphate buffer solution for removing unadsorbed fraction (Fc+7S fraction). Then, the adsorbed protein (Fab fraction) was eluted with the buffer solution to which sodium chloride had been added to a concentration of 0.30M.

Distilled water was added to the Fc+7S fraction, and the resulting solution was made up 0.005M phosphate buffer solution. The solution was poured into a DEAE-cellulose column which had been equilibrated with the buffer solution. The column was washed with the same buffer solution to remove unadsorbed fraction. Then the adsorbed protein (purified Fc fraction) was eluted with the same buffer but added with sodium chloride to a concentration of 0.30M.

The Fab fraction obtained was subjected again to dialysis against 0.005M phosphate buffer solution (pH 7.5) at 4° C. over a night. A chromatography was repeated with respect to the dialysate, but using DEAE-cellulose column and the 0.005M phosphate buffer solution. The purified Fab fraction was obtained as an unadsorbed fraction.

The Fab and Fc fragments each obtained above were dissolved in a 0.05M Tris-HC buffer solution (pH 8.2) to a concentration of about 2%. Then, 2-mercaptoethanol was added to the solution to a final concentration of 0.75 to 5.25 M to sever the disulfide bonds.

The resulting solution was then mixed with 0.75 to 5.25 M iodoacetic acid, allowed to react for 1 hour while the pH being kept at 8.0, and then treated with a Sephadex ® G-25 column to remove the reductant and alkylation reagent. Then the solution was dialyzed against physiolocial saline. The dialyzate was filtered aseptically and then lyophilized.

Reference Example 2 (Digestion with papain)

To a 2.5% solution of IgG (20 ml, EDTA-0.05M phosphate buffer solution, pH 7.5) was added 5 mg of papain. Digestion was carried out at 37° C. for 10 to 20 minutes, and then the mixture was cooled with ice-water. The cooled mixture was centrifuged to remove insolubles, and the supernatant was fractionated by using a Sephadex ® G-150 column to obtain the 3.5S fraction. The fraction was treated with dithiothreitol of a final concentration of 0.14M at room temperature for 2 hours at pH 7.5 to 8.0. Then, iodoacetamide was added to the treated product to a final concentration of 0.2M, and the mixture was allowed to react for 1 hour with ice-cooling. The reaction mixture was dialyzed against a 0.005M Tris-HCl solution, pH 8, and the dialyzate containing a crystalline product formed was subjected to centrifugation. The precipitated fraction comprised alkylated Fc fragments, while the supernatant comprised crude alkylated Fab fragments. The latter was subjected to Sephadex ® G-150 column chromatography, ion-exchange chromatography and the like to give purified alkylated Fab fragments. On the other hand the former was recovered as an alkylated Fc fragment.

Example 1 (Preparations for oral administration)

| (1) | Alkylated Fab fragment or alkylated Fc fragment | 5.0 mg |
| --- | --- | --- |
| (2) | "Fine particle No. 209 for direct tabletting" (mfd. by Fuji Chemicals Co.) | 46.6 mg |
| (3) | Crystalline cellulose | 24.0 mg |
| (4) | CM-cellulose | 4.0 mg |
| (5) | Magnesium stearate | 0.4 mg |

A powder mixture formed of the above ingredients was tabletted to give tablets each weighing 80 mg.

Example 2 (Injections for intravenous administration)

| (1) | Alkylated Fab fragment or alkylated Fc fragment | 50 mg |
| --- | --- | --- |
| (2) | Glucose | 100 mg |
| (3) | Physiological saline | 10 ml |

A mixed solution formed of the above ingredients was filtered through a membrane filter, then filtered again aseptically, and the filtrate was dispensed aseptically into vials. The vials were filled with nitrogen and then hermetically sealed to give injections for intravenous administration.

Example 3 (Capsules)

| (1) | Alkylated Fab fragment or alkylated Fc fragment | 50 g |
| --- | --- | --- |
| (2) | Lactose | 935 g |
| (3) | Magnesium stearate | 15 g |

A uniform powder mixture formed of the above ingredients was filled in 200 mg portions into hard-gelatin capsules.

Example 4 (Liposome preparations)

The alkylated Fab and Fc fragments were each dissolved in a 0.01M phosphate buffer solution, pH 7.2, containing 0.125M NaCl, to a concentration of about 0.5 %. Separately, 100 mg portions of egg-yolk phospholipio containing respectively 0, 5, 10 and 20% (W/W) of phosphatidic acid were each dissolved in 10 ml of chloroform, and each solution was treated in a rotary evaporator to give a film of the phospholipids. To the film, was added 1 ml of the solution of alkylated Fab or Fc fragments mentioned above, and the mixture was shaked to form liposomes, whereby alkylted Fab and Fc fragments were each incorporated threinto to give a liposome preparation.

What is claimed is:

1. A composition for the treatment of gastrointestinal ulcers comprising an effective amount of an alkylated Fab fragment or an alkylated Fc fragment, of human IgG together with a pharmaceutically acceptable diluent, wherein the alkyl moiety is selected from the group consisting of a lower alkyl, an N,N-dilower-alkylcarbamide-lower-alkyl, a lower-alkoxycarbonyl-lower-alkyl, a carboxy-lower-alkyl, a cyano-lower-alkyl, an ω-amino-lower-alkyl and a benzoyl-lower-alkyl.

2. The composition of claim 1, wherein the alkyl moiety is carboxymethyl.

3. The composition of claim 1, wherein the alkylated Fab or Fc fragment is obtainable by reducing the Fab or Fc fragment or mixture of the both with a reducing agent to sever disulfide bonds therein and alkylating the reduced product.

4. The composition of claim 1 in the form of powders, tablets, capsules or liposome preparations for oral administration.

5. The composition of claim 1 in the form of liquid preparations for intravenous, intramuscular or oral administration.

6. A method for treating a gastrointestinal ulcer which comprises administering an effective amount of a composition according to claim 1.

* * * * *